United States Patent [19]

Hillion et al.

[11] 4,357,478

[45] Nov. 2, 1982

[54] PROCESS FOR HYDROGENATING UNSATURATED COMPOUNDS

[75] Inventors: Gerard Hillion, Herblay; Christian Lassau, Villepreux, both of France

[73] Assignee: Institut Francais du Petrole, Rueil-Malmaison, France

[21] Appl. No.: 152,961

[22] Filed: May 23, 1980

Related U.S. Application Data

[63] Continuation-in-part of Ser. No. 864,070, Dec. 23, 1977, abandoned.

[30] Foreign Application Priority Data

Dec. 24, 1976 [FR] France .................................. 76 39218

[51] Int. Cl.³ ......................... C07C 29/19; B01J 31/02
[52] U.S. Cl. .................................... 568/816; 585/250; 252/429 C; 252/431 C
[58] Field of Search ....................... 252/429 C, 431 C; 585/250; 568/816, 814

[56] References Cited

U.S. PATENT DOCUMENTS

| 3,412,174 | 11/1968 | Kroll | 252/431 C |
| 3,454,644 | 7/1969 | Dewhirst | 585/250 |
| 3,591,649 | 7/1971 | Kroll et al. | 252/431 C |
| 3,784,481 | 1/1974 | Lassau et al. | 252/429 C |
| 3,943,067 | 3/1976 | Chan et al. | 252/429 C |
| 3,946,087 | 3/1976 | Hillion et al. | 568/881 |
| 4,066,571 | 1/1978 | Columberg | 252/431 C |

FOREIGN PATENT DOCUMENTS

| 1904613 | 9/1969 | Fed. Rep. of Germany | 252/431 C |
| 2421934 | 11/1974 | Fed. Rep. of Germany | 252/431 C |

Primary Examiner—Natalie Trousof
Assistant Examiner—James H. Reamer
Attorney, Agent, or Firm—Millen & White

[57] ABSTRACT

Unsaturated compounds are hydrogenated in the presence of a catalyst obtained by reacting an organoaluminum compound with a transition metal carboxylate and an organic carboxylic acid.

13 Claims, No Drawings

PROCESS FOR HYDROGENATING UNSATURATED COMPOUNDS

This application is a continuation-in-part of our patent application Ser. No. 864,070 filed Dec. 23, 1977, now abandoned.

The invention has for object a new process for hydrogenating unsaturated compounds in liquid phase, said process being characterized by the use of a soluble catalyst obtained by reacting an organometal reducing compound with at least one transition metal carboxylate and at least one strong carboxylic acid.

It was already known to prepare hydrogenation catalysts by contacting a transition metal compound with a reducing compound, for example an alkoxyaluminum hydride or a trialkylaluminum. See for example U.S. Pat. Nos. 3,663,635 or 3,784,481. The Chemical and Engineering News publication of Mar. 4, 1963, pages 34–35, discloses the preparation of catalysts by reacting tri-isobutyl aluminum with chromium stearate or manganese acetate. According to the author, the solubility of these catalytic systems is doubtful in opposition to that of the catalytic systems prepared from an acetylacetonate, for example, chromium acetylacetonate or manganese acetylacetonate. Notwithstanding this advantage of solubility, the acetylacetonates are not widely used, in view of their high cost.

The activity of the catalysts of doubtful solubility, obtained from carboxylates, is not entirely satisfactory, particularly as concerns the reaction velocity.

It has been discovered, and this is the object of the present invention, that an excellent catalyst for hydrogenating unsaturated compounds in homogeneous phase or substantially homogenous phase can be obtained by reacting an organometal reducing agent with at least one transition metal carboxylate and at least one strong carboxylic acid, the molar ratio of the strong carboxylic acid to the transition metal carboxylate being from 0.05:1 to 1:1. With such a catalyst, the reaction velocity is generally increased.

A strong carboxylic acid is an organic carboxylic acid whose $pK_a$ in water at 25° C. is lower than 7. In case of a too low solubility in water, the $pK_a$ is determined by using correlations between the $pK_a$ of the other carboxylic acids determined in water and in an alcohol such as methanol or ethanol. As a rule, these are acids with 1 to 25 carbon atoms, preferably 6 to 25 carbon atoms, per molecule and which contain only hydrogen, carbon and oxygen; weak organic acids, such as alcohols, glycols, amines and diketones (acetylacetone) are thus excluded.

Examples of strong organic acids which can be used according to the invention are: hexanoic, heptanoic, iso-heptanoic, octanoic, decanoic, palmitic, stearic, naphthenic, toluic and oleic acids.

A preferred general formula of these acids is R—COOH, where R is a hydrocarbyl radical of 5 to 24 or more carbon atoms. R may be substituted with groups which are not detrimental to the reaction, for example, —OH, —CO— or additional —COOH groups.

The preferred transition metals are cobalt and, above all, nickel. These metals may be associated to other transition metals having a co-catalytic effect, as described for example in the Belgian Pat. No. 813,996 or French Pat. No. 2,249,709.

A metal carboxylate, and particularly a cobalt or nickel carboxylate, is a salt of one of these metals with one of the above carboxylic acids of $pK_a$ lower than 7.

Examples of carboxylates are cobalt diacetate, nickel diacetate, a nickel naphthenate, nickel stearate, cobalt ethylhexanoate, nickel benzoate, nickel decanoate and nickel oleate. Examples of additional salts are iron, zinc, molybdenum or zirconium stearate or heptanoate. The carboxylates from acids with 6–25 carbon atoms are preferred.

These compounds are usually employed as solutions in solvents which may be, for example, a saturated, unsaturated or aromatic hydrocarbon, a mixture of these hydrocarbons or an ether.

The reducing compound is a tri-hydrocarbylaluminum compound of the formula Al $R_1 R_2 R_3$, where each of $R_1$, $R_2$ and $R_3$ is a hydrocarbyl radical.

Non-limitative examples are triethylaluminum or triisobutylaluminum.

The reducing compound may be used in the pure state or in a solvent, for example a hydrocarbon or an ether.

The method of manufacture of the catalyst is not critical. For example, the solution of the metal carboxylate may be poured into a solution of the reducing compound, or the solution of the reducing compound may be poured into the solution of the metal carboxylate, or the solution of the reducing compound is poured into a solution of the first carboxylate and a solution of the second carboxylate is then added. The reducing compound may be introduced into a common solution of the carboxylic acid and the carboxylate (s), or the carboxylic acid is added to the reaction production of the carboxylate (s) with the reducing agent. The catalyst is preferably prepared in an inert solvent, in the absence of the compound to be hydrogenated. An active catalyst may be sometimes prepared in the presence of the compound to be hydrogenated or the reaction product. The inert solvent is preferably an aliphatic or cycloaliphatic saturated hydrocarbon or an aromatic hydrocarbon (the latter preferably at moderate temperature).

The ratio of the number of molecules of the reducing compound to the number of atoms of the transition metal is generally between 0.5:1 and 10:1, preferably between 1.5:1 and 6:1.

The manufacture of the catalyst may be effected, for example, at 0°–200° C., preferably 70°–160° C. This manufacture may be carried out in an inert atmosphere, for example under nitrogen or hydrocarbon gas or in a reducing atmosphere, for example under hydrogen pressure. The latter method is preferred, provided the hydrogen partial pressure is at least 0.1 kg/cm². The so-prepared catalysts retain their activity over a long period, eventually one year or more. This beneficial effect appears to be attributable to hydrogen stabilisation of the catalyst during manufacture thereof.

When using the so-obtained catalyst, the hydrogen pressure may range from 0.1 to 100 bars, preferably from 2 to 50 bars.

The reaction temperature may range from 0° to 300° C., preferably 10° to 250° C.

The concentration of the catalyst is usually low, from 5 to 1,500 ppm, preferably 20 to 1,000 ppm by weight of metal with respect to the total feedstock.

The ratio by volume of the injected catalytic solution to the volume of the compound to be hydrogenated is usually between 0.001% and 10%.

Depending on the operating conditions, the hydrogenation may be partial or total; in particular, a selective partial hydrogenation may be obtained when conducting a hydrogenation reaction in several successive steps.

The unsaturated hydrogenable compounds are particularly hydrocarbons with 2–40, for example 2–20, carbon atoms, irrespective of the number and the type of unsaturation, such as acetylenic, ethylenic, polyolefinic and aromatic hydrocarbons, and unsaturated compounds having one or more oxygen or nitrogen atoms, in addition to the carbon and hydrogen atoms, such as saturated and unsaturated ketones, unsaturated esters, saturated and unsaturated aldehydes, unsaturated alcohols and others, saturated and unsaturated nitriles, unsaturated sulfones, unsaturated amines, imines, saturated and unsaturated nitro derivatives, or phenols. Unsaturated polymers may also be hydrogenated, for example polybutadiene or polyisoprene.

Examples of hydrogenable compounds are butadiene, cyclododecatriene, vinylacetylene, cyclopentadiene, butenes, cyclopentene, benzene, alkylbenzenes, phenol and its derivatives, alkyldiphenyls, alkylnaphthalenes, for example toluene, xylenes, methylnaphthalene, propionitrile, adiponitrile, oleonitrile, 1,4-dicyanobutene, benzonitrile, vinylethylsulfone, vinylethylketone, unsaturated fatty oils and ethyl linoleate.

When operating continuously, it is more advantageous to inject the previously prepared catalytic solution into the duct for feeding the compound to be hydrogenated, for example propylene, butadiene, benzene or naphthalene, rather than directly into the reaction vessel.

When operating in continuous manner, the hydrogenation product may be discharged by vaporisation. The latter technique is particularly advantageous when the reaction product is, for example, propane, butenes, butane or cyclohexane. This product may be vaporized and then condensed. A fraction of the exhausted catalyst may be discharged continuously or periodically, as desired. It is however sometimes advantageous to let the catalyst accumulate in the reaction vessel.

According to another preferred operating manner, a reactor containing fixed catalyst is arranged after one or more reactors operated in homogeneous phase as above described; the reaction thus terminates in heterogeneous phase, either in gas phase or in liquid phase.

The catalyst may be used in a batch process or in a continuous process.

The following examples illustrate the invention in a non-limitative manner. In these examples, the reaction velocity is the average velocity for a 90% conversion of the starting material.

Sodium stearate is prepared by reacting sodium hydroxide with stearic acid. After washing, sodium stearate is dissolved into water and nickel chloride hydrate is then added; a green precipitate of nickel stearate is then collected; results of the elementary analysis conform to the theoretical values. This general method of preparation of the salts of transition metals has also been used in the following examples, with other carboxylic acids, to prepare nickel or cobalt salts.

COMPARATIVE EXAMPLE 1

0.6 millimole of nickel stearate is dissolved in 10 millimeters of benzene. A solution of triethylaluminum in benzene is added in a molar nickel/aluminum ratio of 3. The resulting solution is used as catalyst to hydrogenate benzene at 180° C. under 7 atm. hydrogen pressure. The catalyst concentration, expressed as nickel, is 35 millimoles per liter. The reaction is terminated in 2 hours. Cyclohexane is obtained quantitatively.

COMPARATIVE EXAMPLE 2

Example 1 is repeated, except that nickel stearate is replaced by the nickel salt of decanoic acid in the same molar proportion. The result is unchanged.

COMPARATIVE EXAMPLE 3

A catalyst is made from 1.4 millimole nickel octoate, 0.35 millimole iron octoate and 5.6 millimole triethylaluminum; it is used to hydrogenate 100 g of bis-phenol A dissolved in 100 g of 2-ethyl hexanol at 170° C. under 23 bars hydrogen pressure. After 5 hours of reaction, hydrogen is no longer absorbed, the theoretical hydrogen amount being already absorbed. Dicyclohexanol propane is obtained quantitatively.

EXAMPLE 4

Example 2 is repeated, except that decanoic acid is added to the solution of the nickel salt in a molar ratio of the acid to nickel of 0.2. The reaction is terminated within 45 minutes. The cyclohexane yield is quantitative.

EXAMPLE 5

Example 3 is repeated, except that octoic acid is added to the nickel and iron solution in a molar ratio of the acid to the metal (nickel+iron) of 0.20. The absorption of hydrogen ceases after 4 hours of reaction and dicyclohexanol propane is obtained quantitatively.

EXAMPLE 6

Example 4 is repeated, except that the solvent of the nickel salt is a 50:50 mixture of di-isopropyl ether and benzene. The reaction is terminated within 35 minutes. The cyclohexane yield is quantitative.

EXAMPLE 7

Example 4 is repeated, except that the solutions of the metal salt and of the reducing agent are admixed under a hydrogen pressure of 0.2 to 0.3 bar. The result is unchanged.

EXAMPLE 8

Example 4 is repeated, except that the catalyst has been stored for 1 year before use. The reaction is terminated within 60 minutes. The cyclohexane yield is quantitative.

EXAMPLE 9

Example 7 is repeated, except that the catalyst was prepared one year earlier. The result remains unchanged.

What is claimed is:

1. In a process for hydrogenating a hydrogenatable unsatuated organic compound having carbon-carbon, carbon-oxygen, carbon-nitrogen or nitrogen-oxygen multiple bonds, in substantially homogeneous, organic liquid phase, wherein said compound is hydrogenated with hydrogen, in the presence of a hydrogenation catalyst which is substantially soluble in said organic liquid phase, the improvement which comprises using as said catalyst the product obtained by reacting at least one tri-hydrocarbyl aluminum reducing agent with (a) at least one carboxylate of a transition metal and (b)

at least one organic carboxylic acid whose p$K_a$ in water at 25° C. is lower than 7.

2. A process according to claim 1, wherein the transition metal carboxylate (a) is a nickel or cobalt carboxylate or a mixxture of nickel and iron carboxylates.

3. A process according to claim 1, wherein the organic carboxylic acid comprises 6 to 25 carbon atoms.

4. A process according to claim 1, wherein the carboxylate (a) is a derivative of a carboxylic acid with 6–25 carbon atoms.

5. A process according to claim 1, wherein the molar ratio of the carboxylic acid to the transition metal carboxylate is from 0.05:1 to 1:1.

6. A process according to claim 1, wherein the tri-hydrocarbyl aluminum is tri-ethyl aluminum.

7. A process according to claim 1, wherein the tri-hydrocarbyl aluminum is tri-isobutyl aluminum.

8. A process according to claim 1, wherein the catalyst concentration is 5 to 1500 ppm by weight of metal with respect to the total feedstock.

9. A process according to claim 1, wherein the catalyst has been prepared under a hydrogen partial pressure of at least 0.1 kg/cm$^2$.

10. A catalyst for use in the process of claim 1, which consists of the reaction product of at least one tri-hydrocarbyl aluminum with (a) a transition metal carboxylate and (b) an organic carboxylic acid whose p$K_a$ in water at 25° C. is lower than 7.

11. A catalyst according to claim 10, wherein the organic acid comprises 6 to 25 carbon atoms and the carboxylate is a transition metal salt of an organic carboxylic acid whose p$K_a$ in water is lower than 7 at 25° C.

12. A catalyst according to claim 10, wherein said transition metal carboxylate is a nickel or a cobalt carboxylate or a mixture of nickel and iron carboxylates.

13. A catalyst according to claim 10, wherein said catalyst is prepared under a hydrogen partial pressure of at least 0.1 kg/cm$^2$.

* * * * *